United States Patent [19]
Volcy et al.

[11] Patent Number: 6,011,616
[45] Date of Patent: Jan. 4, 2000

[54] SYSTEMS AND METHODS FOR MEASURING THE CONCENTRICITY OF A CORE TO A FERRULE

[75] Inventors: Jerry R. Volcy, Tucker; Calvin J. Martin, Atlanta; Walter S. Konik, Lilburn, all of Ga.

[73] Assignee: Lucent Technologies, Inc., Murray Hill, N.J.

[21] Appl. No.: 09/166,060

[22] Filed: Oct. 2, 1998

[51] Int. Cl.[7] ................................................. G01N 21/00
[52] U.S. Cl. ............................................. 356/73.1; 385/60
[58] Field of Search .................................. 356/73.1, 426, 356/399, 400; 382/141, 151, 152, 288; 385/59, 60, 71, 76, 89

[56] References Cited

U.S. PATENT DOCUMENTS

| | | |
|---|---|---|
| 4,738,507 | 4/1988 | Palmquist . |
| 4,738,508 | 4/1988 | Palmquist . |
| 4,825,092 | 4/1989 | Mehadji ................................. 356/400 |
| 4,992,666 | 2/1991 | Robertson ............................. 250/561 |
| 5,367,372 | 11/1994 | DiVita et al. . |
| 5,408,309 | 4/1995 | Shimada et al. . |
| 5,572,313 | 11/1996 | Zheng et al. . |
| 5,649,036 | 7/1997 | Anderson et al. ..................... 356/73.1 |
| 5,657,131 | 8/1997 | Csipkes et al. . |
| 5,729,622 | 3/1998 | Csipkes et al. . |

OTHER PUBLICATIONS

Wayne R. Moore; "Foundations of Mechanical Accuracy;" 1970; pp. 17–19; First Edition; The Moore Special Tool Company; Bridgeport, Connecticut, USA.

G. Warnes and C.A. Miller; "A Study of Core–Concentricity Error Measurement and the Implications for Monomode Systems;" May 1–3, 1984; pp. 138–144; SPIE vol. 468; Fibre Optics '84.

L. Moura and R. Kitney; "A Direct Method for Least–Squares Circle Fitting;" Computer Physics Communications; Apr. 24, 1990; pp. 57–63; vol. 64; Elsevier Science Publishers B.V., North–Holland.

*Primary Examiner*—Frank G. Font
*Assistant Examiner*—Tu T. Nguyen

[57] ABSTRACT

Systems and methods for quickly and accurately measuring the concentricity of a core with respect to a ferrule are provided. A beam splitter arrangement is utilized to separately image both the core and the ferrule outer edge using separate imagers. The two images are combined through coordinate transformation so that the offset of the core with respect to the ferrule center can be determined.

24 Claims, 9 Drawing Sheets

SYSTEMS AND METHODS FOR MEASURING THE CONCENTRICITY OF A CORE TO A FERRULE

FIELD OF THE INVENTION

The present invention generally relates to fiber optic communications, and more particularly, to fiber optic connectors.

BACKGROUND OF THE INVENTION

Fiber optic networks are being deployed at an ever-increasing rate due, at least in part, to the large bandwidth provided by fiber optic cables. Inherent with any fiber optic network design is the need to connect individual optical fibers to other optical fibers and to equipment. A common technique for connecting optical fibers is by terminating an optical fiber with a ferrule, and bringing the ferrule into a mating relationship with another ferrule terminating a second optical fiber. This type of connection is referred to as a ferrule connection. Examples of ferrule connection systems can be found in U.S. Pat. Nos. 4,738,507 and 4,738,508, both issued to Palmquist and assigned to the assignee of the present invention.

When two optical fibers are connected to one another, such as by a ferrule connection, there exists a potential for loss of optical power due to an imperfect transfer of the optical signal from one optical fiber to the other. The loss can be attributed to a number of different factors, but is most commonly caused by a lateral, or transverse, offset in the co-axial alignment of the passageways defined by the ferrules, hereinafter referred to as the cores. In fact, aligning the cores of two ferrules is a formidable task due to the extremely small size of the cores, which can be as small as 8–9 micrometer ($\mu$m) in diameter. To further complicate the task of co-axially aligning the cores with exacting precision is the fact that the core of a ferrule is typically slightly offset from the center of the ferrule as a result of the manufacturing process of the ferrule. This offset is often referred to as the concentricity (also referred to as eccentricity) of the core with respect to the ferrule, and includes an angular component and a magnitude component. The angular component provides the direction of the offset, while the magnitude component provides an absolute distance between the ferrule center and the core center.

Accordingly, in connecting two optical fibers together, a coupling device, which typically includes a sleeve, is utilized to co-axially align the cores by engaging the alignment surfaces of the respective ferrules. The sleeve is generally a rigid cylindrical structure, as described in U.S. Pat. No. 4,378,508, cited hereinbefore. However, the great disparity in the size of the ferrule and the core makes the alignment of the cores difficult. As previously mentioned, the core may be as small as 8–9 $\mu$m in diameter, whereas the ferrule may be 1,250–2,500 $\mu$m in diameter. Moreover, the misalignment of the cores may be caused by the concentricity error of the respective cores, which may reduce the amount of light energy transmitted between the two optical fibers. For example, if the two cores being connected are offset in opposite directions, then the core overlap will be minimized when the ferrules are placed end-to-end. It is desirable to align the cores within 1 $\mu$m, though certain applications require the core be aligned within 0.3 $\mu$m.

A solution to the offset problem is the tunable connector. A tunable connector is constructed so that the ferrule can be rotated within the ferrule housing and secured in more than one position, typically in three or more positions. For instance, the LC™ fiber optic connector manufactured by Lucent Technologies, Inc., USA, is tunable into six equally spaced positions that are approximately 60° apart. Alternatively, the SC connector is tunable into four equally spaced positions, approximately 90° apart. Thus, the offset of the core center with respect to the ferrule center is determined, and then the ferrule is adjusted so that the offset is in a predetermined direction. Therefore, the cores are offset in substantially the same radial plane with respect to the longitudinal axis of the cores, which may increase the overlap between the two cores. However, tunable connectors require precise and reliable methods for determining the offset so that the connectors are accurately tuned.

Several methods have been proposed for accurately measuring the offset of a core with respect to a ferrule center, a few of which are discussed below.

The first method involves viewing the core under a high-powered microscope while the ferrule is rotating within a fixture, such as a V-shaped support block. The movement of the core is measured as the ferrule is rotated about its longitudinal axis. The locus of points defining the center of the core is, in general, circular as the ferrule is rotated, and the radius of the circle is equal to the concentricity error. The aforementioned technique is described in more detail in U.S. Pat. No. 4,738,508, cited hereinbefore.

A second method focuses upon measuring the effect of the offset and involves interconnecting the ferrule under test to a reference connector, sometimes referred to as a "golden connector," which is known to have a negligible concentricity error. After establishing the connection with a coupling structure, the light transmission there through is measured. The offset is determined based upon the loss of light and one or more mathematical equations that define the light loss as a function of the offset.

A third method for measuring the concentricity error involves the imaging of the core and several boundary or edge segments of the ferrule end face. A center for the ferrule and a center for the core are determined based upon the acquired images, and the core offset is determined therefrom, as described in greater detail in U.S. Pat. No. 5,729,622 issued to Cspikes et al. All-optical methods of measuring concentricity such as the one suggested in Cspikes et al. generally have been difficult to implement because of the large disparity between the size of the core and that of the ferrule (usually at least two orders of magnitude).

While the aforementioned methods have some merit, several require physical movement of the ferrule which causes undesirable wear of the testing equipment, several are operator dependent and labor-intensive, yet others are computationally intensive, and require expensive equipment. Accordingly, a heretofore unsatisfied need exists in the industry for a system and method of precisely measuring the concentricity error of an optical fiber ferrule that is less labor-intensive, less computationally intensive, less expensive, and more reliable than presently known systems.

SUMMARY OF THE INVENTION

The present invention provides for systems and methods for quickly and accurately measuring the concentricity of a fiber core with respect to a ferrule. The present invention is particularly well suited for implementation in the manufacturing of optical fiber connectors, and more particularly, in a tuning station for tuning optical fiber connectors. The present invention utilizes a beam splitter arrangement to separately image both the core and ferrule using separate cameras. The two images are combined through coordinate transformation so that the offset of the core with respect to the ferrule center can be determined. Advantageously, there are no moving parts which may wear or degrade over time, nor are the results operator dependent. Further, the present invention provides methods and systems for measuring concentricity that are relatively fast and inexpensive and which have good thermal and mechanical stability.

In accordance with an aspect of the present invention, a system for measuring concentricity of a core of a ferrule generally comprises an image acquisition system for imaging the core and ferrule separately, and an imaging processing system for determining the concentricity based on the images captured by the image acquisition system. The image acquisition system includes a core imager and a ferrule imager, and wherein the core imager records an image of the core and a ferrule imager records an image of the entire outer edge of the ferrule. The images of the core and ferrule from the core imager and ferrule imager, respectively, are presented to the image processing system.

The image processing system determines the center of the core from the core image and the center of the ferrule from the ferrule image, and determines therefrom the concentricity of the core center with respect to the ferrule center. The image processing system may include a computer readable medium whose contents cause the image processing system to process the core image to determine the coordinate location of the center of the core, and to process the ferrule image to determine a coordinate location of the center of the ferrule. The computer readable medium may further cause the image processing system to translate the coordinate locations of the core and the ferrule centers into a single coordinate system, from which the concentricity can be accurately determined.

The imaging system may comprise a first magnification lens for magnifying the image of the core, and a second magnification lens for magnifying the image of the ferrule, wherein the first magnification lens has a greater magnifying power than the second magnifying lens. Alternatively, a first lens may magnify both the core and ferrule images by a first magnitude, and a second lens may further magnify the core image. The imaging system may further include a digitizer that converts the analog signal from the core imager into a digital signal, and that converts the analog image from the ferrule imager into a digital signal.

A reference device of known geometry may be imaged by the core imager and the ferrule imager to calibrate a transformation relationship between the core imager and the ferrule imager, also referred to herein as the mechanical misalignment error. In a preferred embodiment, the reference device is a fiber optic connector with a ferrule of known core concentricity.

In accordance with another aspect of the present invention, the method for measuring concentricity of a core of a ferrule generally comprises the steps of imaging the core with a core imager, imaging the entire outer edge of the ferrule with a ferrule imager, determining a center of the core based on the image of the core, determining a center of the ferrule based on the image of the ferrule, and determine the concentricity of the core of the ferrule based on the center of the core and the center of the ferrule. The step of imaging the core may include the step of magnifying the core by first magnitude, and the step of imaging the ferrule may include simply magnifying the ferrule image by a second magnitude, wherein the core image is magnified to a greater degree than the ferrule image. The steps of imaging the core and imaging the ferrule may be preformed simultaneously using a beam-splitter which channels the image of the core to the core imager and the image of the ferrule to the ferrule imager. In this configuration, the device under test is on the optical axis of a core imager, and the beam-splitter passes the device under test image through to the core imager while the beam-splitter redirects a portion of the image of device under test to the ferrule imager Also, a reference device may be imaged by the core imager and the ferrule imager by placing the reference device on the optical axes of the ferrule imager Alternatively, a second beam-splitter may be utilized to channel the image of a reference device onto the optical axes of the core imager.

The method of measuring concentricity may include the step of transforming the coordinates of the core center or the coordinates of the ferrule center into the coordinate frame of the other. The coordinate transformation may include the step of rotating the coordinates so that they are in the same field of view. In addition, the coordinate transformation may include the step of scaling the center coordinates according to a relationship between the core imager and the ferrule imager, as determined during calibration.

The systems and methods for measuring concentricity of a core of a ferrule in accordance with the present invention have many advantages, few examples of which are set forth hereafter.

An advantage of the present invention is that it provides for contactless and non-destructive measurement of the concentricity of a core of a ferrule.

Another advantage of the present invention is that it provides for fully automatic measurement of an offset of a core of a ferrule that is relatively fast.

Another advantage of the present advantage is that it provides for the measurement of the core offset with a very high accuracy of typically within ±100 nanometers ($\mu$m).

Another advantage of the present invention is that it provides for the measurement of the concentricity of the core of a ferrule without any adjustment or movement by the operator, thereby reducing operator error.

Another advantage of the present invention is that it can be implemented with relatively less expensive equipment than the prior art solutions.

Other features and advantages of the present invention will become apparent to one skilled in the art upon examination of the following drawings and detailed description. It is intended that all such features and advantages be included herein within the scope of the present invention, as defined by the appended claims.

BRIEF DESCRIPTION OF THE DRAWINGS

The present invention can be better understood with reference to the following drawings. The elements of the drawings are not necessarily drawn to scale, emphasis instead being placed upon clearly illustrating the principles of the present invention. Furthermore, like reference numerals designate corresponding parts throughout the several views.

DETAILED DESCRIPTION OF PREFERRED EMBODIMENTS

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Many modifications and other embodiments of the invention will come to mind to one skilled in the art to which this invention pertains having the benefit of the teachings presented in the foregoing descriptions and the associated drawings.

Figure 1:
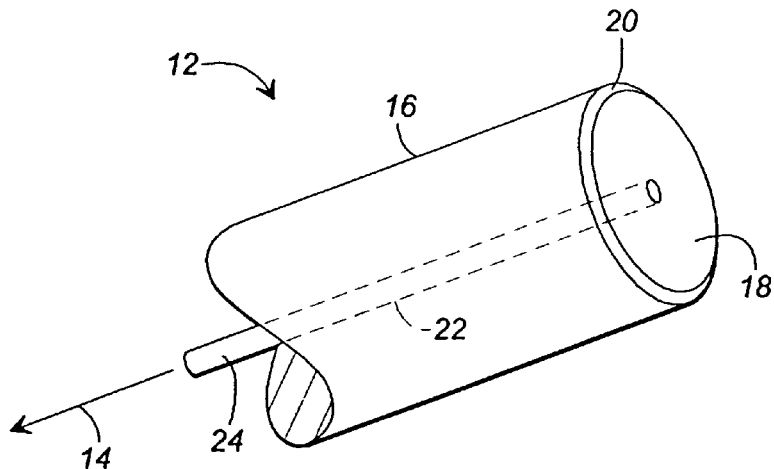
FIG. 1 is a perspective view of a ferrule of the type conventionally used in fiber optic cable terminations.

With reference to FIG. 1, a ferrule 12 (also referred to as a ferrule termination) of the type commonly used to terminate optical fiber cable is illustrated. The ferrule termination 12 is generally cylindrical in shape along its longitudinal axis 14, as defined by an alignment surface 16 at its outermost edge. A ferrule end face 18, which is substantially perpendicular to the longitudinal axis 14 of the ferrule termination 12, is connected to the alignment surface 16 by a beveled chamfer 20. The ferrule 12 further includes a central core (or passageway) 22 that substantially surrounds an optical fiber 24, as well known to those skilled in the art. The ferrule termination 12 is typically made of a ceramic material, though other suitable materials may be utilized.

Figure 2:
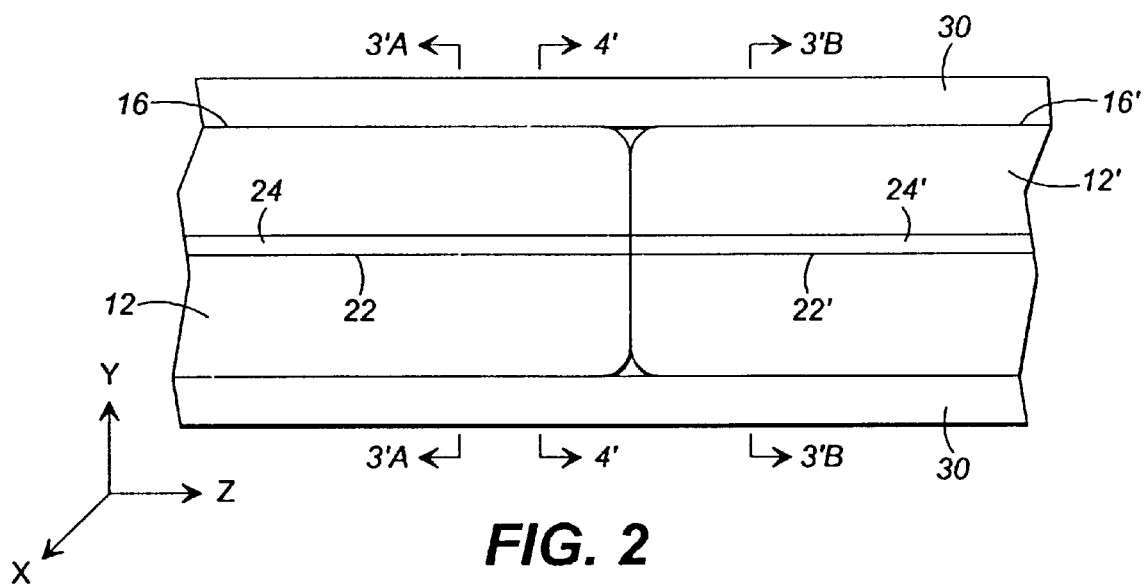
FIG. 2 is a cross-sectional view of a coupling structure for connecting and aligning separate ferrules of respective optical fibers.

In a connection of two ferrules 12,12' for purposes of optically connecting the two optical fibers 24, 24', the two ferrules 12, 12' are placed in an end-to-end configuration so that the cores 22 and 22' are precisely co-axially aligned, as illustrated in FIG. 2. The ferrules 12, 12' are joined and held in place by a coupling structure 30, which generally comprises a cylindrical sleeve made of a ceramic material, or the equivalent thereof. An example of a coupling structure having a cylindrical sleeve is described in the U.S. Pat. No. 4,738,508, cited hereinbefore. As shown, the coupling structure 30 engages the alignment surfaces 16,16' of the respective ferrules 12, 12', so that the alignment of cores 22 and 22' is precisely maintained. In order to maintain a low loss connection between optical fibers 24, 24', it is desirable to have cores 22 and 22' precisely aligned with one another so that the maximum amount of optical energy is transferred between the optical fibers 24, 24'.

Figure 3A:
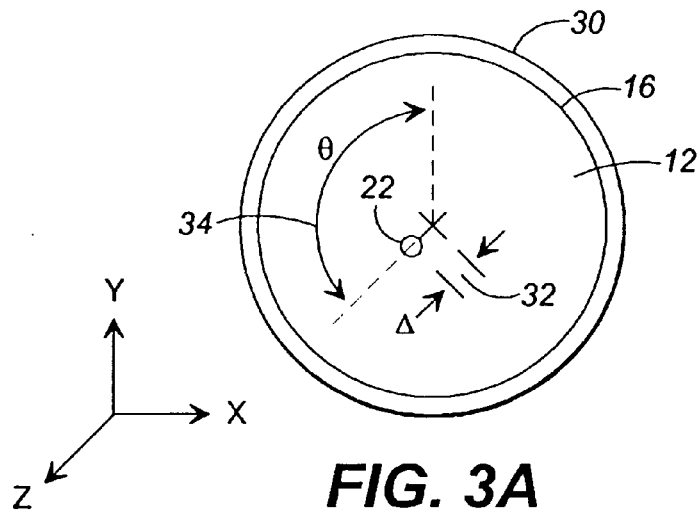
FIG. 3A is a longitudinal view of a first ferrule within the coupling structure taken along line 3a'—3a' of FIG. 2.

Accordingly, it is desirable that the core of each ferrule be concentric with the ferrule center. However, due to manufacturing error, the cores are often offset from the ferrule termination centers. As illustrated in FIGS. 3A, the offset or eccentricity of any core can be quantified as a distance Δ, denoted by reference numeral 32, and an angle θ taken in a counterclockwise direction from the vertical Y-axis, denoted by reference numeral 34. The angle θ is approximately 135° in FIG. 3A. It is noted that the size of the cores 22, 22' with respect to the ferrules is greatly exaggerated in the figures for illustrative purposes, as is the offset distance Δ.

Figure 3B:
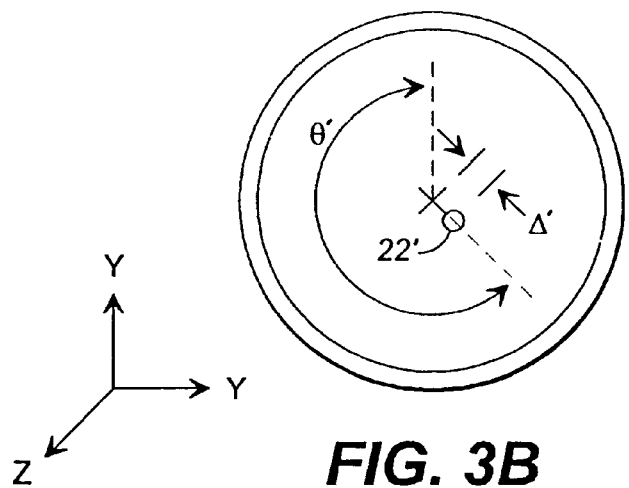
FIG. 3B is a longitudinal view of a second ferrule within the coupling structure taken along line 3b'—3b' of FIG. 2.
Figure 4:
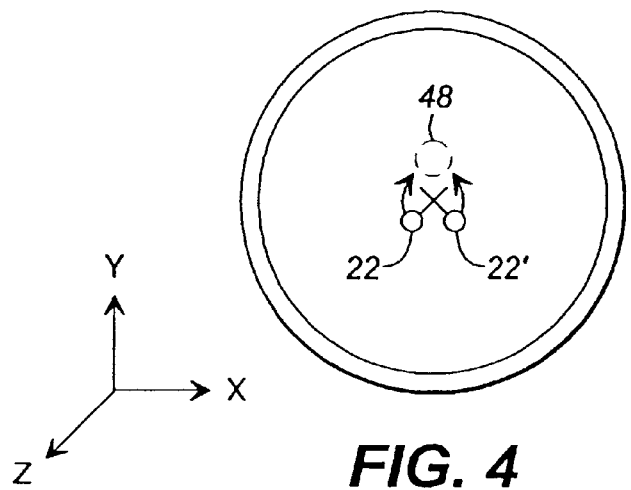
FIG. 4 is a longitudinal view of the misalignment between the cores of the first and second ferrules of FIGS. 3A and 3B, respectively, taken along line 4'—4' of FIG. 2.

If, for instance, the core 22' of ferrule termination 12' was offset a distance Δ' that was substantially equal to Δ (ie., Δ=Δ'), and an angle θ'=210° in a counterclockwise direction from the vertical Y-axis, as illustrated in FIG. 3B, then with the two cores 22 and 22' would be misaligned as shown FIG. 4. However, by tuning (i.e., rotating) ferrules 12, 12' so that the respective offsets are in a predetermined direction, the cores 22, 22' become substantially aligned at a hypothetical location 48, as illustrated in FIG. 4, and the optical energy transfer between the optical fibers 24, 24' can be increased because of the improved core alignment.

Figure 5:
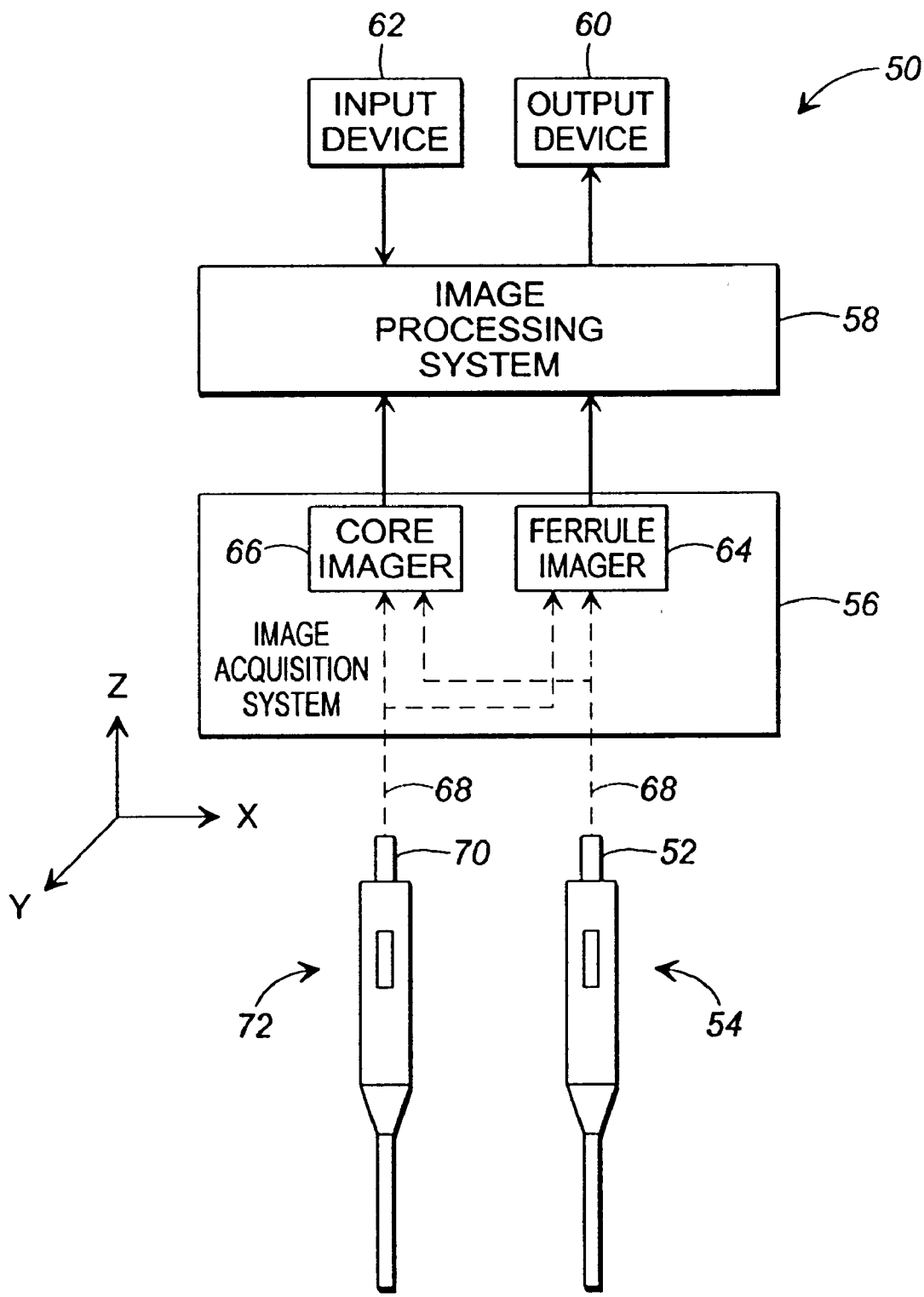
FIG. 5 is a block diagram illustrating a concentricity and measurement system of the present invention.

In accordance with the present invention, an optical concentricity measurement system 50 is provided, as illustrated in FIG. 5. The optical concentricity measurement system 50 is configured to measure the concentricity of a core of a ferrule 52 associated with the ferrule frame 54, referred to hereinafter as the device under test (DUT). The optical concentricity measurement system 50 includes an image acquisition system 56 and an image processing system 58. Optionally, an output device 60 and input device 62 may be employed and connected to the image processing system 58 for presenting information to the user or receiving information from the user, respectively. For example, the output device 60 may be a conventional display or printer, or other suitable mechanism for supplying information to the user. For example, the output device 60 may be utilized to display to the user the concentricity (i.e., offset) of the core as numerical representations of the distance and angle, and/or to display the images of the core and the ferrule edge. The input device 62 can be any suitable mechanism for receiving prompts or information from the user and conveying the information to the image processing system 58, such as a keyboard or mouse. In addition, the output and/or input device 60, 62 may be connected to other systems for automation of the connector tuning process, for communicating with other systems, or for data collection.

The image acquisition system 56 utilizes a ferrule imager 64 and core imager 66 to image the ferrule 52. The ferrule 52 is placed on the optical axis 68 of the ferrule imager 64 and the core imager 66. The ferrule imager 64 images the entire cylindrical outermost boundary or edge of the ferrule 52, as typically defined by the alignment surface thereof. The core imager 66 images the core of the ferrule 52. The core imager and the ferrule imager may be any suitable imaging device for converting an optical signal into an electrical signal, such as a charged-coupled device (CCD). The image acquisition system 56 then passes electronic signals indicative of the core image and ferrule image to the image processing system 58.

The image processing system 58 receives the electronic signals comprising the core image and ferrule image from the image acquisition system 56, and initially digitizes the images for further processing. Correction for any aspect ratio distortion caused by the digitization of the images is preferably corrected before any substantive processing of the images so that the processing will not have to take the aspect ratio distortion into consideration. The image processing system 58 then determines the coordinates of the center of the core from the core image, and coordinates of the center of the ferrule from the ferrule image. The coordinates of the center for either the core or the ferrule are then transformed into the other's coordinate frame so that the core center to the ferrule center are in the same coordinate system. Thus, while the core and ferrule outer edge are imaged separately, the abstract coordinates of the two images are subsequently combined mathematically to determine the core offset. In the preferred embodiment, the coordinates of the core center are transformed to the ferrule frame.

The transformation of the coordinates of the core center is achieved using a scaling factor derived from the calibration of the optical concentricity measurement system 50 using an object of known geometry, such as another ferrule termination 70 of ferrule frame 72, referred to hereinafter as the reference device. As with the DUT 54, the reference device 72 is placed on the optical axis 68 of the ferrule imager 64 and the core imager 66 so that the ferrule termination 70 can be imaged by both. By mapping one of the core image or ferrule image to the other, and knowing the actual offset of termination ferrule 70, a scaling factor can be determined between the core imager 66 and ferrule imager 64. By performing this calibration prior to each concentricity measurement, excellent mechanical and thermal stability can be achieved.

First Embodiment

Figure 6:
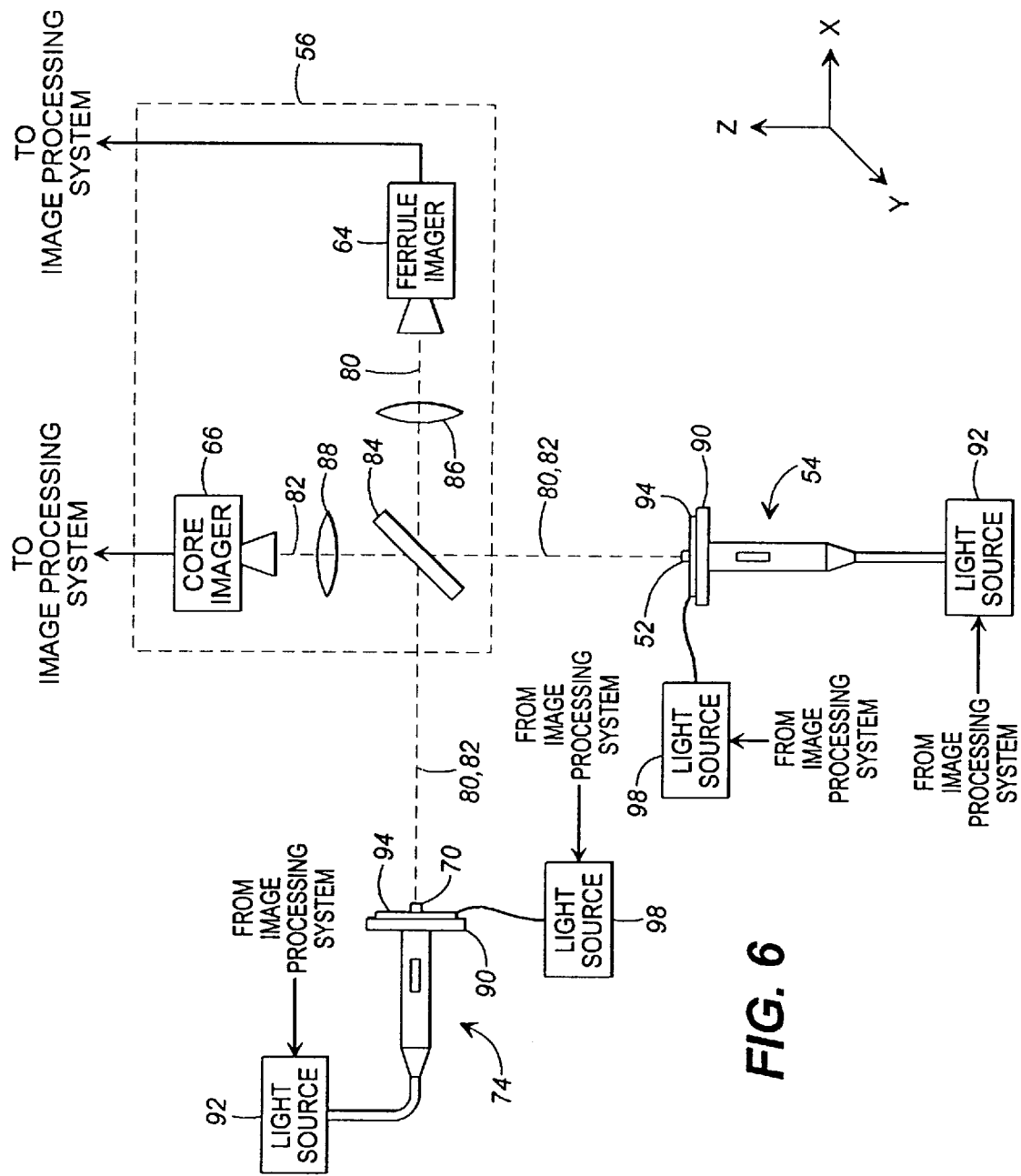
FIG. 6 is a schematic block diagram illustrating a first embodiment of a concentricity measurement system in accordance with the present invention.

In accordance with the first embodiment of the present invention, the image acquisition system 56 comprises a ferrule imager 64 having an optical axis 80 and a core imager 66 having an optical axis 82, as illustrated in FIG. 6. A beam splitter 84 combines the optical axis 80, 82 so that both the ferrule imager 64 and the core imager 66 may image the ferrule 52 of the DUT 54 and ferrule termination 70 of the reference device 74. Preferably, the beam splitter 84 is a partially reflecting mirror. Thus, the beam splitter 84 splits the image of the ferrule 52 of the DUT 54, and channels a portion of the image onto the optical axis of the ferrule imager 64 and a substantially equal portion of the image onto the optical axis of the core imager 66. In addition, the beam splitter 84 splits the image of the ferrule 70 of the reference device 74, and channels a portion of the image onto the optical axis of the ferrule imager 64 and a substantially equal portion of the image onto the optical axis of the core imager 66.

A first objective lens 86 is placed in the optical path 80 of the ferrule imager 64 for magnifying the image of the ferrule outer edge so that more accurate measurements can be made. Likewise, a second objective lens 88 is placed in the optical path 82 of the core imager 66 for magnifying the image of the core. Advantageously, by magnifying the images separately, the optics of the two imagers 64,66 are independent, resulting in a more stable system. The optical images are magnified before being captured by the imagers so the recorded images are represented by a greater number of image pixels, thereby increasing the resolution of the image. However, magnification of the image results in an inherently noisy and uncrisp image, not to mention the effect of dust and surface aberrations. This problem is dealt with using a recursive point-rejection technique, as described in detail below. The image of the ferrule outer edge is preferably magnified by factor of approximately 9.5X, and the image of the core is preferably magnified by a factor of approximately 760X.

As previously mentioned, the ferrule imager 64 and core imager 66 may be any suitable imaging devices, but are preferably a CCD Model KPM3U from Hitachi-Denshi Limited, Japan. Generally, a CCD camera comprises a pixel array for receiving an image and encoding the image by generating an analog voltage signal proportional to the intensity of the light comprising the image at each pixel of the CCD, as is well known in the art. It is noted that since the ferrule end face is on a different focal plane than the outermost edge of the ferrule, the ferrule imager 64 and core imager 66 should be independently focusable.

A connector seat 90 is utilized for holding the DUT 54 so that the ferrule 52 is consistently and precisely positioned on the optical axes 80, 82. The exact positioning of the connector seat 90 may be achieved by iteratively adjusting the position of the connector seat 90 while imaging a ferrule situated within the connector seat 90 until the ferrule can be accurately imaged as a circle. In particular, if the image of the ferrule is an oblong ellipse, then the ferrule is vertically misaligned from the optical axis of the imager, whereas if the ferrule appears as a prolonged ellipse, then the ferrule is horizontally misaligned with respect to the optical axis of the imager. Once a circular image is achieved, the connector seat 90 can be secured in place.

Figure 7:
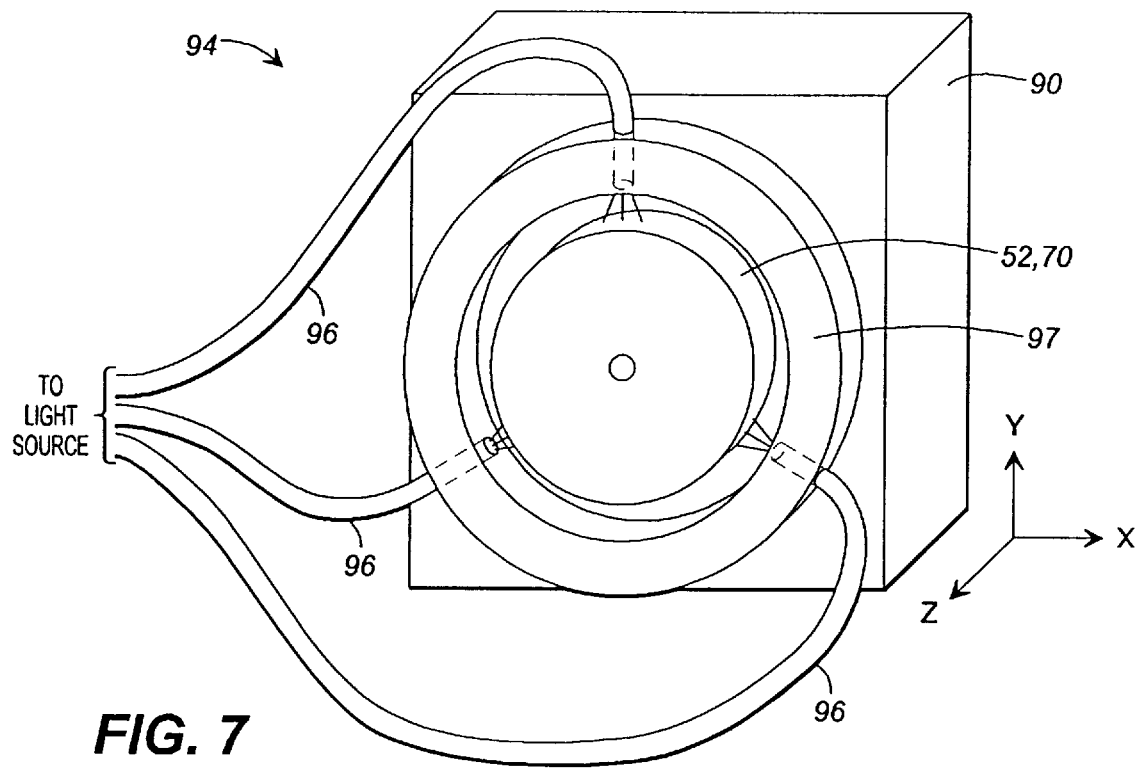
FIG. 7 is a front elevational view of a lighting apparatus for illuminating a ferrule for imaging.

The cores of the respective ferrules 52, 70 are illuminated by light sources 92 which launch light through the cores, as well know in the industry. An example of a suitable light source is the Optispec Core Light, Model ME2000 by Micro Enterprises, Inc., Norcross, Ga. The ferrules 50, 70 are illuminated by miniature ring lights 94 which may, for example, comprise illuminated fiber optic bundles 96 which are equally spaced about a ring shaped frame 97 for illuminating ferrules 52, 70, as illustrated in FIG. 7. The fiber optic bundles 94 may be illuminated by light launched from light sources 98, such as Model DCRII by Fortec, Inc., Auburn, N.Y. The actuation and brightness of the light sources 92, 98 are individually controlled by the image processing system 58. For example, the core light and ring light associated with the DUT 54 may be illuminated and the core light and ring light associated with the reference device 74 may be turned off so the ferrule imager 64 and core imager 66 will only see the DUT 54. Likewise, the ring light and core light associated with the DUT 54 may be turned off while the ring light and core light of the reference device 74 may be turned on so the ferrule imager and the core imager will only see the reference device. Further, the amount of illumination of the respective cores and ferrules is controlled by the image processing system 58, which may be useful for various reasons such as focusing the imagers.

Figure 8:
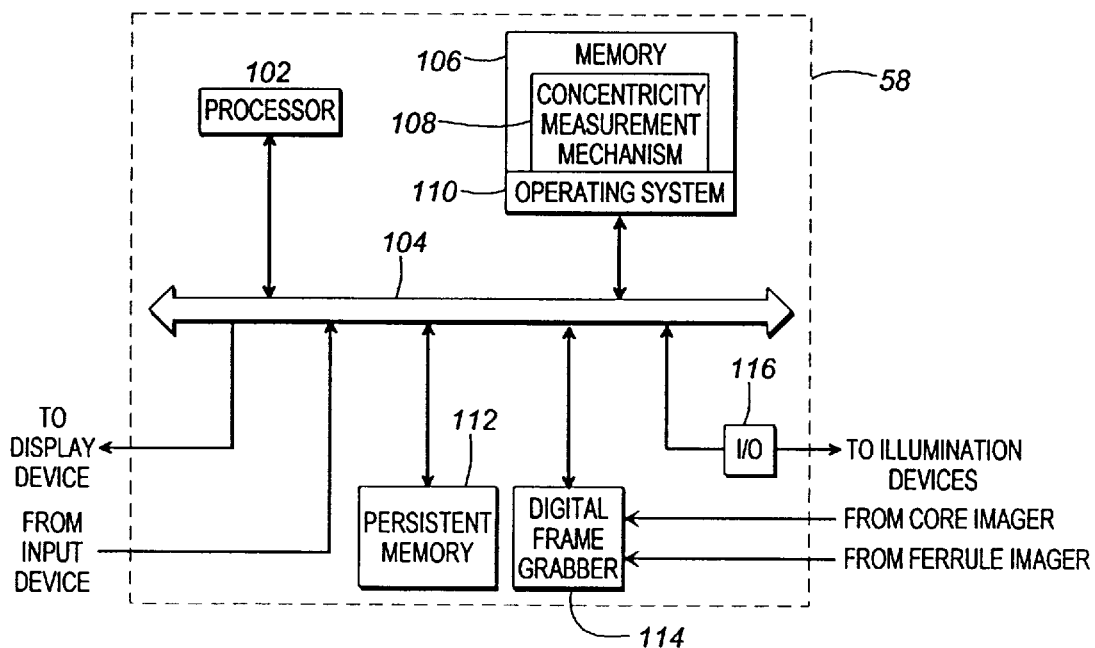
FIG. 8 is a block diagram of one embodiment of the imaging processing system of FIG. 5.

The image processing system 58 can be implemented by any suitable logic, processor or computer-based system that is configured to process the aforementioned signals from the image acquisition system 56 for determining the concentricity of the core of a ferrule. With reference to FIG. 8, a preferred embodiment of the image processing system 58 comprises a processor 102 that communicates with other elements of the image processing system 58 via a system interface 104. Connected to the system interface is a memory 106 which, in the illustrated embodiment, includes a concentricity measurement mechanism 108 and a conventional operating system 110 that communicates with the processor 102 for facilitating the execution of the concentricity measurement mechanism 108. A persistent memory 112 is provided for storing data and/or executable code, as well known in the art. A digital frame grabber 114 receives analog voltage signals from the image acquisition system 56 which are indicative of the core image and ferrule image. The digital frame grabber digitizes the analog signals for subsequent processing by the concentricity measurement mechanism 108. An example of a commercially available digital frame grabber 114 is Model ICPCI (Rev. AZ) by Imaging Technology, Inc., Bedford, Mass. Lastly, an input/output interface 116 enables control over the actuation and brightness levels of the light sources 92, 98.

The concentricity measurement mechanism 108 may be implemented in software, firmware, hardware, or any combination of software, firmware and hardware. In the preferred embodiment, the concentricity measurement mechanism 108 comprises computer program code that can be executed by a computer or other programmable machine, such as the processor 102, for performing numerous functions including determining a scaling factor for the transformation of coordinates between the core frame and ferrule frame, determining the center of the core, determining the center of the ferrule termination, transforming coordinates between the core frame and the ferrule frame, and determining the concentricity of the core of the ferrule from the coordinates of the core center and the ferrule termination center. As computer program code, the concentricity measurement mechanism 108 may be stored on any computer readable medium for use by or in connection with a computer-related system or method, such as image processing system 58. For purposes of the present disclosure, a computer readable medium is any electronic, magnetic, optical or other physical device or means that can contain or store computer program code for use by or in connection with a computer-related system or method.

Accordingly, the concentricity measurement mechanism 108 determines a centroid of the core from the core image. In essence, the centroid of the core is determined by scanning the core image and determining the average pixel location of the pixels representing the core along the x-axis and the average pixel location of the pixels representing the core along the y-axis. While this method may not be as accurate as other well known methods for determining the center of a feature under examination, it has been determined that the centroid method provides adequate accuracy because of the relatively small dimensions of the core.

However, the centroid method is not particularly well-suited for use with noisy images, such as is the case with the image of the ferrule outer edge. Accordingly, a least-squares circle fitting algorithm is utilized to determine the center of the ferrule termination, as described below. The edges of the ferrule are initially detected using a gradient masked search, which examines the image for a changing gradient between adjacent pixel values. When a gradient change exceeds a predetermined threshold, a data point (i.e., coordinate) representing an edge point is recorded in an array. It is noted that the array of data points may be contaminated by dirt, scratches, and surface roughness in the acquired image of the ferrule.

A prescribed threshold of $D_{MAX}$ is utilized to filter the data in the array. Specifically, the data points that are more than $D_{MAX}$ away from a fitted circle are discarded. This process is repeated recursively until there are no remaining data points more than $D_{MAX}$ away from the last fitted circle. $D_{MAX}$ is empirically determined based on the accuracy desired, and is approximately 1.2 in the preferred embodiment. A final iteration of the least-square algorithm is then applied with all the data points that were previously discarded but which are within $D_{MAX}$ of the last fitted circle in order to recover falsely rejected points. The center of the ferrule can then be calculated from the circle, as well known by those skilled in the art.

Once the centers of the core and the ferrule have been determined, then the concentricity of the core of the ferrule can be determined in the manner described below. In the equations that follow, the superscript C refers to the core and the superscript F refers to the ferrule. The following symbols and abbreviations will be used:

DUT—device under test
REF—reference quantity
MEAS—value as measured
ACT—actual value
MIC—value in microns
$\epsilon$—concentricity
$\theta$—angle of concentricity In addition, the following quantities are assumed to be know:

$\phi$—relative angular orientation between the core imager to the ferrule imager $\epsilon_{REF_{ACT}}$—concentricity of the reference device $\phi_{REF_{ACT}}$—angle of concentricity of the reference device Yet further, for the following equations, it is assumed that the field of view of the ferrule imager 64 is the reference frame, that is, information from images captured by the core imager 66 is mapped to the corresponding ferrule image.

First, before the concentricity of the core of the ferrule can be determined, the precise relationship between the ferrule imager 64 and the core imager 66 is determined during calibration, which is preferably performed before each concentricity measurement. This relationship is learned based on knowledge of the geometry reference device 74 and the relative orientation of the two imagers 64, 66 about the optical axis 80, 82. In the present preferred embodiment, the core imager 66 is rotated 90° on its optical axis with respect to the ferrule imager 64 as a matter of convenience of construction. In the equations to follow, it will be assumed that the angle $\phi$ between these imagers is exactly 90°. Errors in this assumption will map directly onto the final results. However, because most connectors are tunable in sextants (60° intervals) or quadrants (90° intervals), such errors are not critical.

Advantageously, because the relative position of the imagers 64, 66 is learned before every measurement, the thermal and environmental stability of the system is assured to the extent that the geometry of the reference device is stable. The actual relationship between the core imager 64 and the ferrule imager 66 is expressed as a core-to-ferrule scaling factor which represents a pixels per micron difference between the core imager and the ferrule imager resulting from, at least in part the different magnification performed for the different imagers.

The core-to-ferrule scaling factor in can be computed from knowledge of the actual core and ferrule sizes and the size of the images that the core and ferrule produce on imagers 66 and 64, respectively, as expressed in Equation (1) below:

$$\left\{ \begin{array}{c} \text{Core} \\ \text{to} \\ \text{Ferrule} \\ \text{Scale} \end{array} \right\} = \left[ \begin{array}{c} \text{pixels} \\ \text{per} \\ \text{micron} \end{array} \right]_{\text{FERRULE FRAME}} \div \left[ \begin{array}{c} \text{pixels} \\ \text{per} \\ \text{micron} \end{array} \right]_{\text{CORE FRAME}} \quad (1)$$

The orientation of the two imagers 64, 66 is provided for by the core-to-ferrule rotation matrix below, which is a familiar rotation matrix. Thus, the rotation is necessary to compensate for the rotated imagers is expressed in Equation (2) below:

$$\begin{bmatrix} \text{Core} \\ \text{to} \\ \text{Ferrule} \\ \text{Rotation} \\ \text{Matrix} \end{bmatrix} = \begin{bmatrix} \cos\varphi & -\sin\varphi \\ \sin\varphi & \cos\varphi \end{bmatrix} \quad (2)$$

The quantity $$\left\{ x^C_{REF\,MEAS} \quad y^C_{REF\,MEAS} \right\}_{CORE\,FRAME}$$

is the centroid of the core image as measured in the core frame. This quantity is transformed into the ferrule frame through the use of Equation (3) below:

$$\left\{ \begin{matrix} x^C_{REF\,MEAS} \\ y^C_{REF\,MEAS} \end{matrix} \right\}_{FERRULE\,FRAME} = \left\{ \begin{matrix} \text{Core} \\ \text{to} \\ \text{Ferrule} \\ \text{Scale} \end{matrix} \right\} * \begin{bmatrix} \text{Core} \\ \text{to} \\ \text{Ferrule} \\ \text{Rotation} \\ \text{Matrix} \end{bmatrix} \left\{ \begin{matrix} x^C_{REF\,MEAS} \\ y^C_{REF\,MEAS} \end{matrix} \right\}_{CORE\,FRAME} \quad (3)$$

Given the known actual geometry of the reference device 74, a prediction of where the core center should appear on the ferrule image is provided by Equations (4) and (5) below:

$$\begin{bmatrix} x^C_{REF\,ACT} \\ y^C_{REF\,ACT} \end{bmatrix}_{FERRULE\,FRAME} =$$

$$\left\{ \begin{matrix} \text{Ferrule} \\ \text{Microns} \\ \text{per} \\ \text{Pixel} \\ \text{Factor} \end{matrix} \right\} \left\{ \begin{bmatrix} x^C_{REF\,ACT} \\ y^C_{REF\,ACT} \end{bmatrix}_{MIC} + \begin{bmatrix} x^F_{REF\,MEAS} \\ y^F_{REF\,MEAS} \end{bmatrix}_{FERRULE\,FRAME} \right\} \quad (4)$$

where, $$\begin{bmatrix} x^C_{REF\,ACT} \\ y^C_{REF\,ACT} \end{bmatrix}_{MIC} = \begin{bmatrix} \varepsilon_{REF} \cdot \cos\theta_{ACT} \\ \varepsilon_{REF} \cdot \sin\theta_{ACT} \end{bmatrix}_{MIC} \quad (5)$$

Thus, Equations (1) through (5) can be combined in Equation (6) below to determine the center coordinates of the core in the ferrule frame:

$$\begin{bmatrix} x^C_{DUT\,MEAS} \\ y^C_{DUT\,MEAS} \end{bmatrix}_{FERRULE\,FRAME} = \left\{ \begin{matrix} \text{Core} \\ \text{to} \\ \text{Ferrule} \\ \text{Scale} \end{matrix} \right\} * \begin{bmatrix} \text{Core} \\ \text{to} \\ \text{Ferrule} \\ \text{Rotation} \\ \text{Matrix} \end{bmatrix} \left( \begin{matrix} x^C_{DUT\,MEAS} \\ y^C_{DUT\,MEAS} \end{matrix} \right)_{CORE\,FRAME} - \quad (6)$$

$$\left\{ \begin{matrix} x^C_{REF\,MEAS} - x^C_{REF\,ACT} \\ y^C_{REF\,MEAS} - y^C_{REF\,ACT} \end{matrix} \right\}_{FERRULE\,FRAME} + \begin{bmatrix} x^F_{DUT\,MEAS} \\ y^F_{DUT\,MEAS} \end{bmatrix}_{FERRULE\,FRAME}$$

The first group of terms from the left in Equation (6) addresses the rotation and scaling of the core image to make the information compatible with the ferrule image. The second group of terms from the left shifts the core image based on knowledge of the image of the reference device. The last term from the left accounts for any shift of the ferrule image which would necessarily result in a shift of the core images.

The concentricity $\varepsilon$ and concentricity angle $\theta$ can then be determined according to Equations (7) and (8) below:

$$\varepsilon_{DUT\,MEAS}\bigg|_{MIC} = \quad (7)$$

$$\left\{ \begin{matrix} \text{Ferrule} \\ \text{Micron} \\ \text{per} \\ \text{Pixel} \\ \text{Factor} \end{matrix} \right\} \left\{ \sqrt{\left(x^C_{DUT\,MEAS} - x^F_{DUT\,MEAS}\right)^2 + \left(y^C_{DUT\,MEAS} - y^F_{DUT\,MEAS}\right)^2} \right\}_{FERRULE\,FRAME}$$

$$\theta_{DUT\,MEAS} = \tan^{-1}\left[ \frac{y^C_{DUT\,MEAS} - y^F_{DUT\,MEAS}}{x^C_{DUT\,MEAS} - x^F_{DUT\,MEAS}} \right] + \varphi \quad (8)$$

The DUT 54 can then be tuned utilizing the concentricity of the core of the ferrule as determined above. The ferrule may be rotated or tuned manually or by the use of an automated device or machine, such as a robotic arm, so that the offset is in a predetermined direction. Further, the concentricity of ferrules may be used to match ferrules with other ferrules of similar geometries in order to minimize power loss in the fiber optic connection. The information calculated can also be stored in a database or spread sheet for historical performance or benchmarking activities.

Second Embodiment of the Image Processing System

Figure 9:
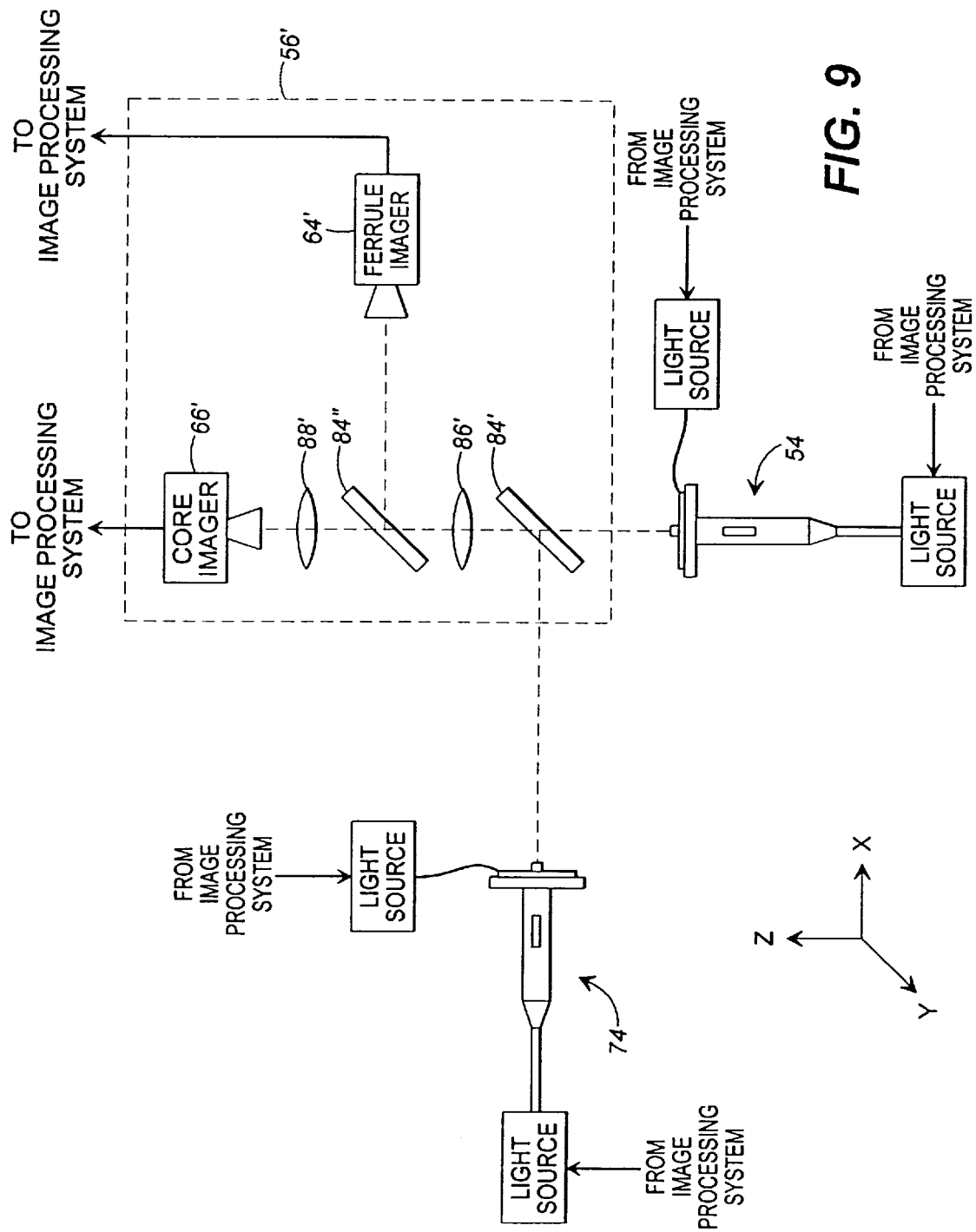
FIG. 9 is a schematic block diagram illustrating a second embodiment of a concentricity measurement system in accordance with the present invention.

With reference to FIG. 9, a second embodiment of the image acquisition system 56' is illustrated. In particular, two beam splitters 84' and 84" are utilized to align the optical axis of the ferrule imager 64' and the core imager 66' for imaging the ferrule and core, respectively, of the DUT 54 and reference device 74. The images of both the core and ferrule are magnified by a first objective lens 86' having a magnification factor of approximately 9.5X. Further, the core image is further magnified by an objective lens 88' before being imaged by core imager 66'. The magnification factor of the objective lens 88' is approximately 80X. In substantially all other respects, the image acquisition system 56' is similar in design and operation to the image acquisition system 56.

The second embodiment is particularly advantageous for use with relatively large core to ferrule diameter ratios. The configuration of the image acquisition system 56' is less restrictive in terms of space, and thus, permits the use of larger, more sophisticated optical components required to achieve crisp images at larger magnifications, as will be appreciated by one of ordinary skill in the art.

Operation

Figure 10:
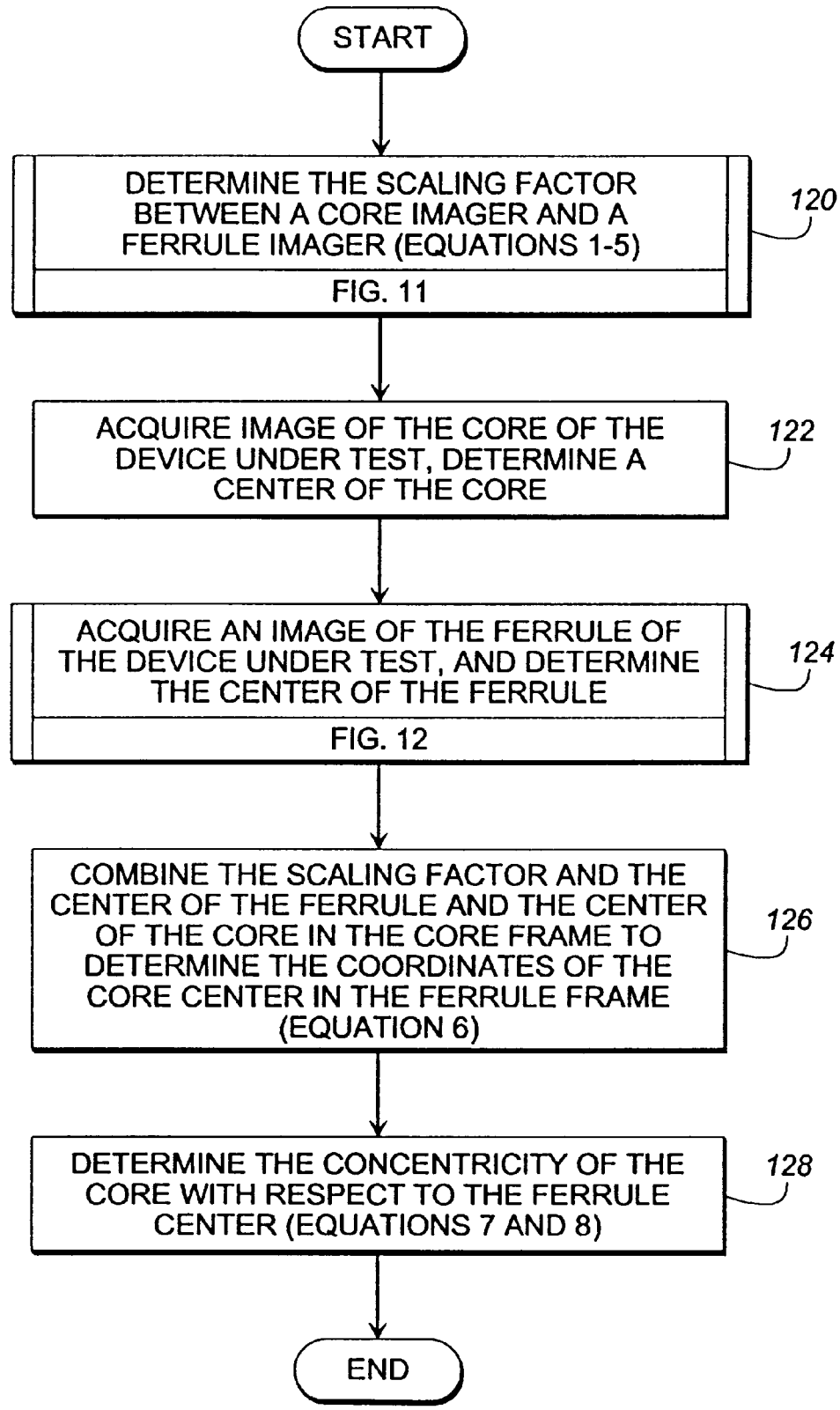
FIGS. 10–12 are flowcharts illustrating a method for measuring the concentricity of a core of a ferrule in accordance with the present invention.
Figure 11:
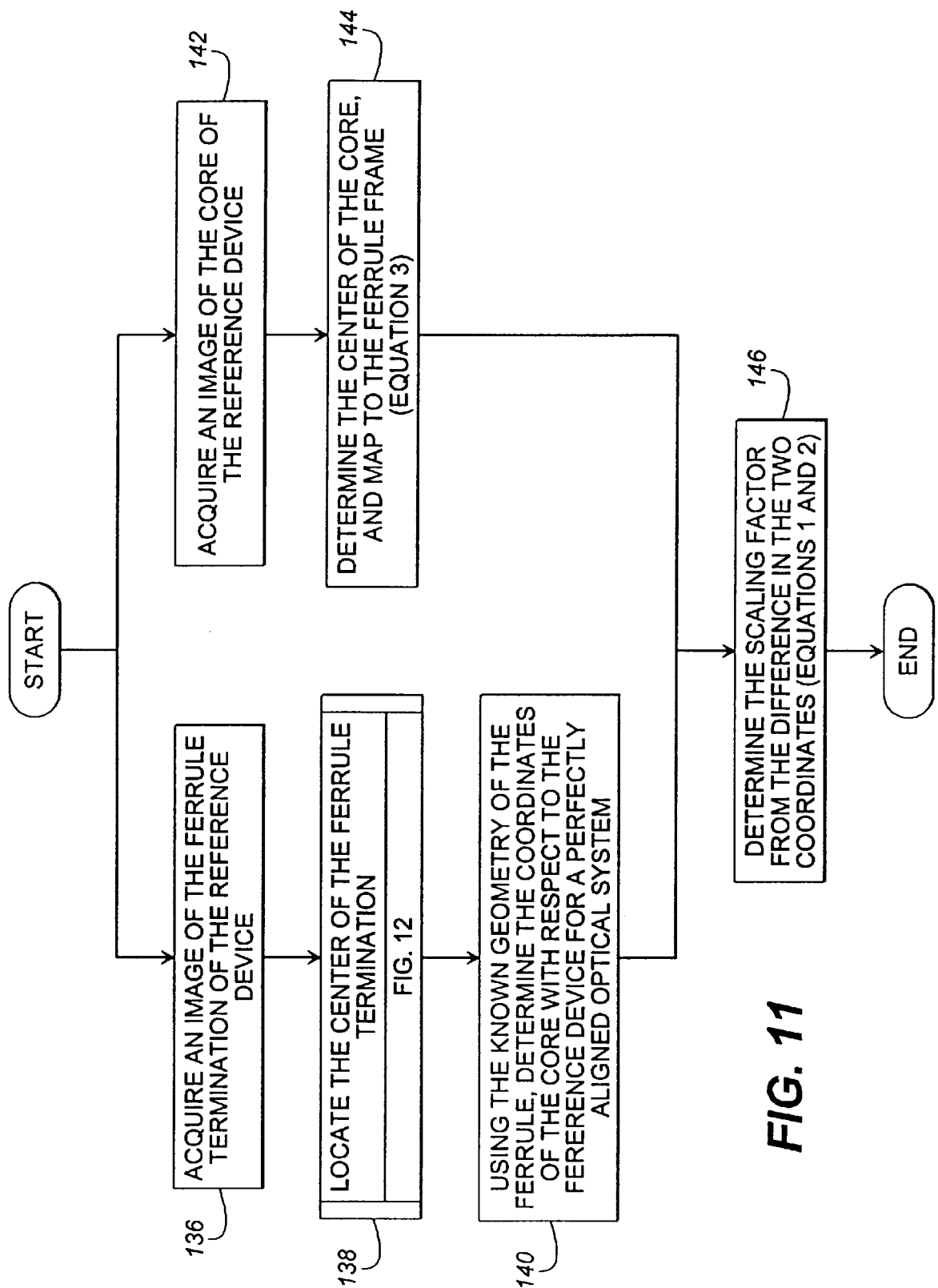
Figure 12:
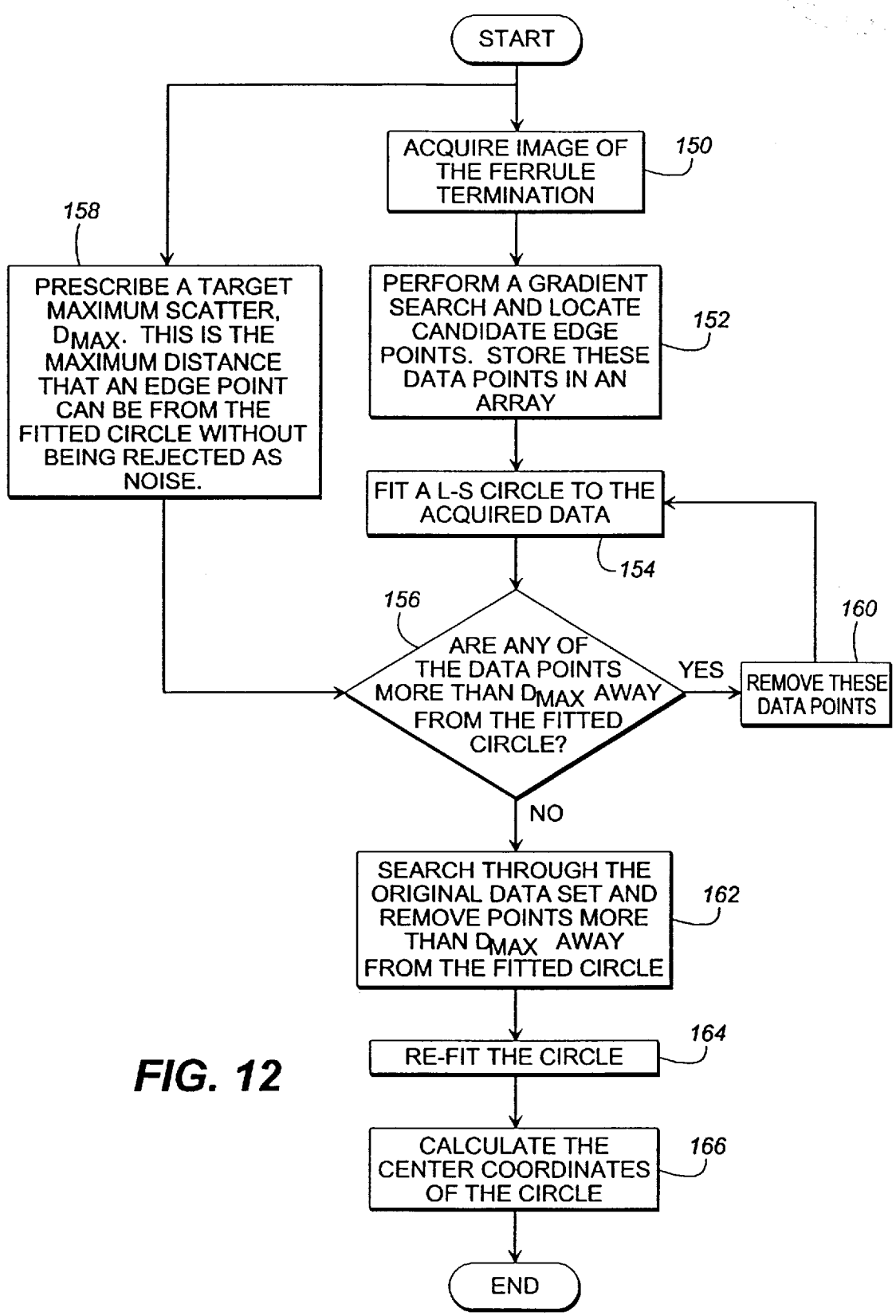

In accordance with the present invention, a method for measuring the concentricity of a core of a ferrule is illustrated in the flowcharts of FIGS. 10–12. With specific reference to FIG. 10, the scaling factor between the core imager and the ferrule imager is initially determined, as indicated by block 120 and as described in further detail with reference to FIG. 11. At block 122, the core of the DUT is imaged, and the center of the core is determined therefrom. An image of the ferrule of the DUT is acquired, and the center of the ferrule is determined, as indicated by block 124 and as further described with reference FIG. 12. At block 126, the scaling factor and the coordinates of the core center and ferrule center are combined to determine the coordinates of the core center in the ferrule frame. It is noted that, in the alternative, the ferrule center may be transformed into the core frame if desired. At block 128, the concentricity of the core with respect to the ferrule is determined based on the coordinates of the core center in the ferrule frame.

With reference to FIG. 11, a method of determining the mechanical alignment error is provided, as described above with reference to Equations (1) through (5). At block 136, the image of the reference device is acquired. The center of the reference device is determined at block 138, and at block 140, the known geometry of the reference device is utilized to determine the coordinates of the core with respect to the ferrule for a perfectly aligned system. In addition, in parallel with blocks 136–140, an image of the reference core is acquired, as indicated by block 142. At block 144, the center of the core is determined, and the coordinates of the center are mapped (i.e., transformed) to the ferrule frame, as described above with reference to Equation (3). At block 146, the scaling factor is determined from the difference in the coordinates of the core calculated at block 140 and 144, as described above with reference to Equations (1) and (2).

With reference to FIG. 12, a method for calculating the center coordinates of the ferrule using a least-square circle fitting algorithm is illustrated. Initially, an image of the ferrule is acquired, as indicated by block 150. A gradient search is performed to locate candidate edge points, which are stored as data points in an array, as indicated by block 152. A least-squares (L-S) circle is fitted to the acquired data in the array, as indicated by block 154. At block 156, it is determined whether any of the data points are more than the threshold $D_{MAX}$ away from the fitted L-S circle. The threshold $D_{MAX}$ is a predetermined threshold of maximum scattered that represents the maximum distance that an edge point can be from a fitted circle without being rejected as noise, as indicated by block 158. If it is determined block 156 that there are data points more than $D_{MAX}$ away from the fitted circle, then those data points are removed, as indicated by block 160, and a next least L-S circle is fitted to the remaining data points at block 154. This recursive point-rejection technique is repeated until it is determined at block 156 that there are no data points more than $D_{MAX}$ away from the fitted circle, at which time the original data set is searched and all data points more than $D_{MAX}$ away from the last fitted circle are removed, as indicated by block 162. With the remaining data points from the original data set, an L-S circle is refitted, as indicated by block 164. At block 166, the coordinates of the center of the fitted circle from block 164 are determined, which represents the center of the ferrule termination.

Many modifications and other embodiments of the invention will come to mind to one skilled in the art to which this invention pertains having the benefit of the teachings presented in the foregoing description and the associated drawings. Therefore, it is understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

Wherefore, the following is claimed:

1. A method for measuring a concentricity of a core to a ferrule, comprising the steps of:

imaging the core of the ferrule;

imaging the entire outer edge of an ferrule;

determining a center of the core based on the image of the core;

determining a center of the ferrule based on the image of the ferrule; and determining the concentricity of the core of the ferrule based on the center of the core and the center of the ferrule.

2. The method of claim 1, wherein said step of imaging the core includes the step of magnifying the core image by a first magnitude and wherein said step of imaging the outer edge of the ferrule includes the step magnifying the outer edge of the ferrule image by a second magnitude, wherein the first magnitude is greater than the second magnitude.

3. The method of claim 1, wherein said step of determining the concentricity of the core includes the step of digitizing the core image and digitizing the ferrule image.

4. The method of claim 1, wherein said step of determining the concentricity includes the step of transforming the coordinates of the core center and the ferrule center into one of a first image frame and a second image frame.

5. The method of claim 4, wherein said step of transforming the coordinates of the core center includes the step of rotating the coordinates so the first frame image and the second frame image are in the same field of view.

6. The method of claim 1, wherein said image of the core is acquired by a core imager and the image of the ferrule is acquired by a ferrule imager, and further comprising the step of calibrating the relationship between the core imager and the ferrule imager.

7. The method of claim 6, wherein said step of calibrating comprises imaging a reference device including a feature of known relative position.

8. The method of claim 7, wherein said step of calibrating includes the step of comparing a measurement of a position of the feature of the reference device with the known relative position of the feature.

9. The method of claim 1, further comprising the step of aligning the ferrule within a connector frame so that the core is radially offset from the center of the ferrule in a predetermined orientation with respect to the connector frame.

10. The method of claim 1, wherein said step of imaging the core and said step of imaging the ferrule are performed substantially simultaneously using a beam splitter which directs a portion of an image of said ferrule and core to one of said core and ferrule imagers.

11. The method of claim 6, wherein said step of imaging the core and said step of imaging the ferrule are performed substantially simultaneously using a first beam splitter that redirects a portion of an image of the ferrule and core to one of the core and ferrule imagers, and a second beam splitter that redirects the image of the reference device parallel with an image of the core and ferrule.

12. A system for measuring a concentricity of a core to a ferrule, comprising:

a core imager that records an image of said core of the ferrule;

a ferrule imager that records an image of an entire outer edge of said ferrule; and an image processing system that determines a first center of said image of said core and a second center of said image of said ferrule, and determines said concentricity of said first center with respect to said second center.

13. The system of claim 12, further comprising a beam splitter that directs said image of said core to said core imager and said image of said ferrule to said ferrule imager.

14. The system of claim 12, wherein said image processing system includes a computer readable medium whose contents cause said image processing system to process said image of said core to determine a coordinate location of a center of said core, and to process said image of said ferrule to determine a coordinate location of a center of said ferrule.

15. The system of claim 14, wherein said content of said computer readable medium further causes said image processing system to translate said coordinate locations of said core and ferrule into a single coordinate system.

16. The system of claim 12, further including a digitizer that converts an image of said core from said core imager from an analog signal into a digital signal, and that converts an image of said ferrule from said ferrule imager from an analog signal into a digital signal.

17. The system of claim 12, further including a first magnification lens for magnifying said image of said core, and a second magnification lens for magnifying said image of said ferrule, wherein said first magnification lens has greater magnifying power than said second magnification lens.

18. The system of claim 12, further comprising a plurality of light sources for selectively illuminating said core and said ferrule.

19. The system of claim 18, wherein said image processing system selectively controls each of said plurality of light sources.

20. The system of claim 12, further comprising a reference device of known geometry that can be imaged by said core imager and said ferrule imager for calibrating a transformation relationship for said core imager and said ferrule imager.

21. The system of claim 20, wherein said reference device is a connector with a ferrule having a known core concentricity.

22. The system of claim 20, further comprising a second beam splitter for redirecting an image of said reference device parallel to an image of said core and ferrule.

23. A system for measuring a concentricity of a core to a ferrule, comprising:

a core imager that records an image of said core of said ferrule, wherein said core imager includes a first optical axis;

a ferrule imager that records an image of said ferrule, wherein said ferrule imager includes a second optical axis, and wherein said first optical axis and said second optical axis are substantially co-axially aligned; and an image processing system that determines a first center of said core from said core image and a second center of said ferrule from said ferrule image, and determines said concentricity of said first center to said second center.

24. The system of claim 24, further comprising a beam splitter that substantially co-axially aligns said first optical axis and said optical axis.

\* \* \* \* \*